United States Patent [19]

Garcia et al.

[11] Patent Number: 5,541,208
[45] Date of Patent: Jul. 30, 1996

[54] INDOLE DITERPENE ALKALOID COMPOUNDS

[75] Inventors: Maria L. Garcia, Edison; Robert A. Giacobbe, Lavellette; Otto D. Hensens, Red Bank; Seok H. Lee, Cranford; Owen B. McManus, North Plainfield; Deborah L. Zink, Manalapan, all of N.J.

[73] Assignee: Merck & Co., Inc., Rahway, N.J.

[21] Appl. No.: 186,197

[22] Filed: Jan. 24, 1994

[51] Int. Cl.6 .................. A61K 31/41; A61K 31/395; C07D 498/22
[52] U.S. Cl. .................. 514/379; 514/410; 548/242; 548/417
[58] Field of Search ................... 548/417, 242; 514/379, 410

[56] References Cited

U.S. PATENT DOCUMENTS

| | | | |
|---|---|---|---|
| 4,374,132 | 2/1983 | Dembinski | 514/379 |
| 4,560,558 | 12/1985 | Parks et al. | 548/242 X |
| 4,812,447 | 3/1989 | Roberts | 514/170 |
| 4,960,867 | 10/1990 | Garcia et al. | 530/324 |
| 4,973,601 | 11/1990 | Dowd et al. | 514/410 |
| 5,006,512 | 4/1991 | Ohnishi | 514/21 |
| 5,006,529 | 4/1991 | Resch | 514/721 |
| 5,130,326 | 7/1992 | Laakso et al. | 514/410 |
| 5,158,969 | 10/1992 | Olesen et al. | 514/419 |
| 5,399,582 | 3/1995 | Dambrowski et al. | 514/410 |

FOREIGN PATENT DOCUMENTS

| | | | |
|---|---|---|---|
| 5331146 | 12/1993 | Japan . | |
| 40-6192264A | 7/1994 | Japan | 548/417 |

| | | | |
|---|---|---|---|
| WO94/09004 | 4/1994 | WIPO | 548/417 |

OTHER PUBLICATIONS

Fischhof, P. K. et al., "Senile Dementia and Calcium Channel Blockers: A Review", Drugs of Today, vol 29, No. 1, (1993) pp. 57–95.

Barton, D. H. R. et al., "A Mild and Efficient Method for the Reduction of Oximes to Imines for Further in situ Reactions", J. Chem. Soc., Chem. Commun., (1984) pp. 337–338.

Selala, M. I. et al., "In Vitro Effects of Tremorgnic Mycotoxins", Journal of Natural Products, vol. 54, No. 1, pp. 207–212, Jan.–Feb. 1991.

Cole, R. J. "Paxilline", Handbook of Toxic Fungal Metabolites, pp. 386–389 (1981) Academic Press.

*Primary Examiner*—Joseph K. McKane
*Attorney, Agent, or Firm*—Francis P. Bigley; Mark R. Daniel

[57] ABSTRACT

The present invention relates to compounds of the formula:

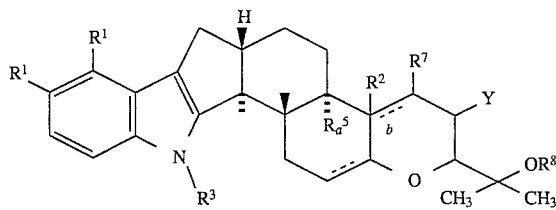

and the pharmaceutically acceptable salts thereof which are useful as potassium channel antagonists, particularly Maxi-K channel antagonists, and thus useful in treating Alzheimer's Disease and other cognitive disorders. This invention is also related to a method of making the compound of formula (I).

6 Claims, No Drawings

INDOLE DITERPENE ALKALOID COMPOUNDS

BACKGROUND OF THE INVENTION

This invention relates to novel indole diterpene alkaloids that are potassium channel antagonists and to processes for making these antagonists and to treating the diseases or disorders associated with malfunction of cellular potassium channels. The invention also relates to chemical intermediates useful in the synthesis of potassium channel antagonists.

The present invention relates to substantially purified novel indole diterpene alkaloids obtained from the fermentation broth of *Nalanthamala sp.* It further relates to synthetic derivatives of the purified isolated alkaloids which are potassium channel antagonists.

The art reveals that a diterpene alkaloid of the formula:

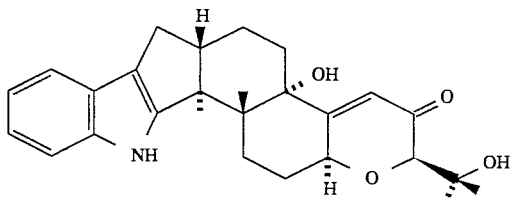

which is known as Paxilline and is produced from a number of microorganisms. Paxilline, and the related compounds paspalitrem and aflatrem are fungal metabolites known to be tremorgens.

Potassium channel antagonists are useful for a number of physiological disorders in mammals, including humans. Ion channels, including potassium channels, are found in all mammalian cells and are involved in the modulation of various physiological processes and normal cellular homeostasis. Potassium ions generally control the resting membrane potential, and the efflux of potassium ions causes repolarization of the plasma membrane after cell depolarization. Potassium channel antagonists prevent repolarization and enable the cell to stay in the depolarized, excited state.

Them are a number of different potassium channel subtypes. Physiologically, one of the most important potassium channel subtypes is the Maxi-K channel which is present in neuronal tissue and smooth muscle. Intracellular calcium concentration ($Ca^{2+}_i$) and membrane potential gate these channels. For example, Maxi-K channels are opened to enable efflux of potassium ions by an increase in the intracellular $Ca^{2+}$ concentration or by membrane depolarization (change in potential). Elevation of intracellular calcium concentration is required for neurotransmitter release. Modulation of Maxi-K channel activity therefore affects transmitter release from the nerve terminal by controlling membrane potential, which in turn affects the influx of extracellular $Ca^{2+}$ through voltage-gated calcium channels. The compounds of the present invention are therefore useful in the treatment of neurological disorders in which neurotransmitter release is impaired.

A number of marketed drugs function as potassium channel antagonists. The most important of these include the compounds Glyburide, Glipizide and Tolbutamide. These potassium channel antagonists are useful as antidiabetic agents. Potassium channel antagonists are also utilized as Class 3 antiarrhythmic agents and to treat acute infarctions in humans. A number of naturally occurring toxins are known to block potassium channels including Apamin, Iberiatoxin, Charybdotoxin, Noxiustoxin, Kaliotoxin, Dendrotoxin(s), mast cell degranuating (MCD) peptide, and β-Bungarotoxin (β-BTX).

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease also is characterized by a diminished neurotransmitter release. Alzheimer's disease is a neurodegenerative disease of the brain leading to severely impaired cognition and functionality. This disease leads to progressive regression of memory and learned functions. Alzheimer's disease is a complex disease that affects cholinergic neurons, as well as serotonergic, noradrenergic and other central neurotransmitter systems. Manifestations of Alzheimer's disease extend beyond memory loss and include personality changes, neuromuscular changes, seizures, and occasionally psychotic features.

Alzheimer's disease is the most common type of dementia in the United States. Some estimates suggest that up to 47% of those older than 85 years have Alzheimer's disease. Since the average age of the population is on the increase, the frequency of Alzheimer's disease is increasing and requires urgent attention. Alzheimer's is a difficult medical problem because there are presently no adequate methods available for its prevention or treatment.

Three classes of drugs are being investigated for the treatment of Alzheimer's disease. The first class consists of compounds that augment acetylcholine neurotransmitter function. Currently, cholinergic potentiators such as the anticholinesterase drugs are being used in the treatment of Alzheimer's disease. In particular, physostigmine (eserine), an inhibitor of acetylcholinesterase, has been used in its treatment. The administration of physostigmine has the drawback of being considerably limited by its short half-life of effect, poor oral bioavailability, and severe dose-limiting side-effects, particularly towards the digestive system. Tacrine (tetrahydroaminocridine) is another cholinesterase inhibitor that has been employed; however, this compound may cause hepatotoxicity.

A second class of drugs that are being investigated for the treatment of Alzheimer's disease is nootropics that affect neuron metabolism with little effect elsewhere. These drugs improve nerve cell function by increasing neuron metabolic activity. Piracetam is a nootropic that may be useful in combination with acetylcholine precursors and may benefit Alzheimer's patients who retain some quantity of functional acetylcholine release in neurons. Oxiracetam is another related drug that has been investigated for Alzheimer treatment.

A third class of drugs is those drugs that affect brain vasculature. A mixture of ergoloid mesylates is used for the treatment of dementia. Ergoloid mesylates decrease vascular resistance and thereby increase cerebral blood flow. Also employed are calcium channel blocking drugs including Nimodipine which is a selective calcium channel blocker that affects primarily brain vasculature.

Other miscellaneous drugs are targeted to modify other defects found in Alzheimer's disease. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Side effects of neuroleptics range from drowsiness and anti cholinergic effects to extrapyramidal side effects; other side effects of these drugs include seizures, inappropriate secretion of antidiuretic hormone, jaundice, weight gain and increased confusion. Anxiolytics, which are mild tranquilizers, are less effective than neuroleptics, but also have milder side effects. Use of these behavior-affecting drugs, however, remains controversial. The present invention is related to novel indole diterpene alkaloids which are useful as potassium channel antagonists. It is believed that certain diseases such as depression, memory disorders and Alzheimers disease are the result of an impairment in neurotransmitter release. The potassium channel antagonists of the present invention may therefore be utilized as cell excitants which should stimulate an unspecific release of neurotransmitters such as acetylcholine, serotonin and dopamine. Enhanced neurotransmitter release should reverse the symptoms associated with depression and Alzheimers disease.

SUMMARY OF THE INVENTION

The present invention relates to compounds of the formula:

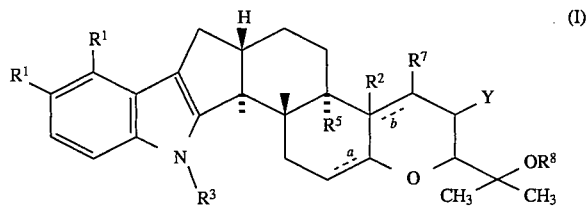

and the pharmaceutically acceptable salts thereof which are useful as potassium channel antagonists, particularly Maxi-K channel antagonists, and thus useful in treating Alzheimer's Disease and other cognitive disorders. This invention is also related to a method of making a compound of structural formula (I).

DETAILED DESCRIPTION OF THE INVENTION

The present invention is directed to novel diterpene alkaloids which are potassium channel antagonists and thus are useful to prevent and treat disorders related to malfunctioning potassium channels in mammalian organisms including humans. In particular, the invention relates to Maxi-K channel antagonists. The present invention further relates to microbiological processes for producing the novel diterpene alkaloids employing the Culture Nalanthalama sp. (MF 5785). This culture has been deposited with the American Type Culture Collection, located at 12301 Parklawn Drive in Rockville, Md. 20852, as ATCC 74192 under the terms of the Budapest Treaty. The invention further relates to synthetic production of potassium channel antagonists wherein a novel process is used to produce novel isoxazolines and to synthetic derivitization of fungal isolates to produce synthetic alkyl esters.

The present invention relates to compounds of the formula:

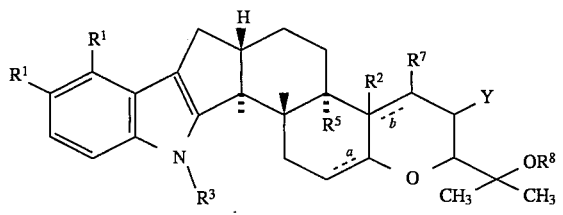

and the pharmaceutically acceptable salts thereof wherein:

$R^1$ is:

(a) H, (b) 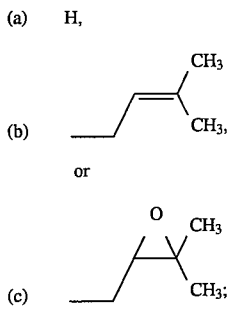

or (c)

$R^2$ and $R^7$ together are oxygen, with the bond between them forming an oxirane ring, or $R^2$ is $CO_2R^4$ and $R^7$ is $OR^6$;

$R^3$ is:
(a) H, or
(b) t-butoxycarbonyl;

$R^4$ is:
(a) H, or
(b) aryl wherein aryl is selected from an unsubstituted phenyl or a phenyl substituted with one or more substituents selected from:
  (1) halogen,
  (2) hydroxy, and
  (3) $C_{1-4}$alkyl;
(c) aryl $C_{1-7}$alkyl, or
(d) $C_{1-7}$alkyl;

$R^5$ is:
(a) H,
(b) OH, or
(c) $OR^6$;

$R^6$ is:
(a) $C_{1-10}$ alkyl,
(b) $C_{1-10}$ alkyloxy$C_{1-10}$ alkyl,
(c) $C_{1-10}$ alkylthio$C_{1-10}$ alkyl,
(d) 2-methoxyethoxy-methyl,
(e) tetrahydropyranyl, or
(f) aryl $C_{1-10}$ alkyl;

Y is bivalent nitrogen and $R^8$ is a single bond to Y forming a 5 membered ring, or Y is bivalent nitrogen or oxygen and $R^8$ is $CH(R^1)$ wherein the carbon is bonded to Y forming a six membered ring, or Y is
(a) H,
(b) OH, or
(c) $OR^6$, and $R^8$ is $C_{1-10}$ alkyl or $C_{1-10}$ alkenyl;

indicates a double bond is optionally present at a or b.

The present invention further relates to compounds and the pharmaceutically acceptable salts thereof of the formula:

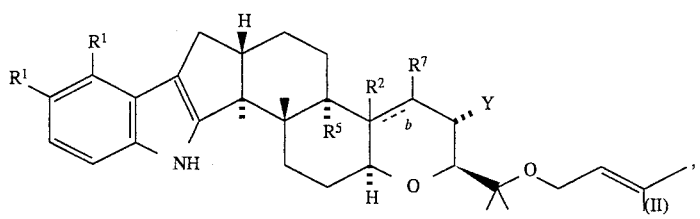
(II)
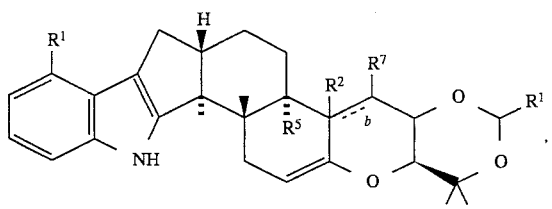
(III)
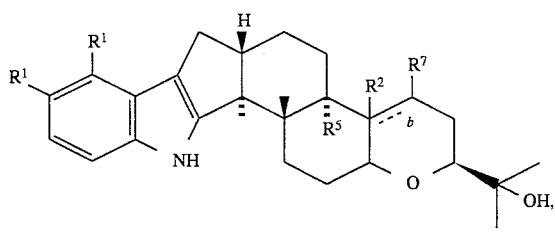
(IV)
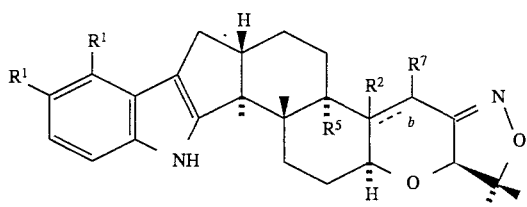
(V)
and
The present invention further relates to compounds and the pharmaceutically acceptable salts thereof of the formula:
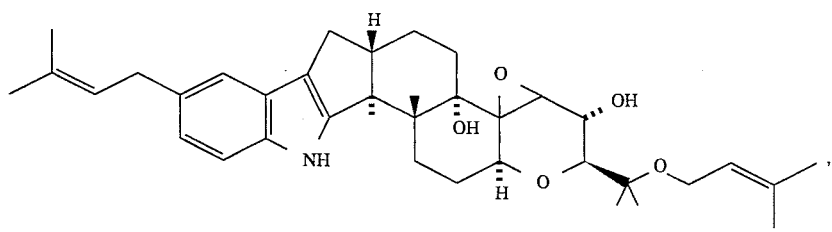
Compound A
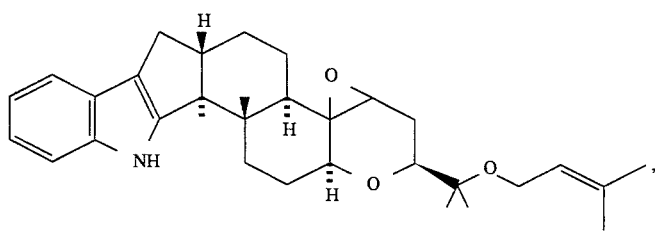
Compound B
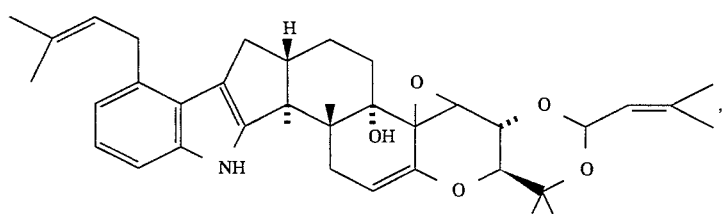
Compound C

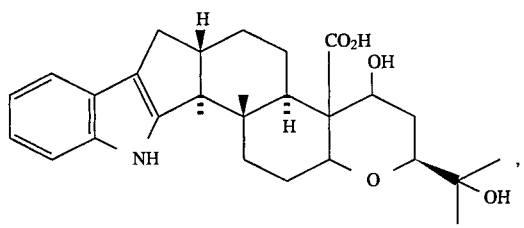

Compound D

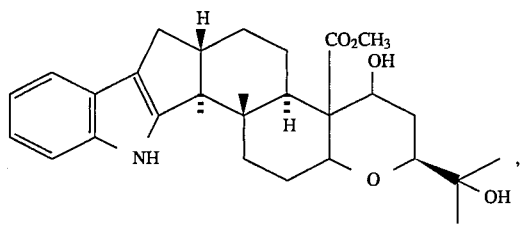

Compound E

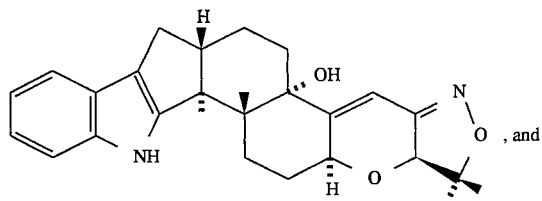

Compound F

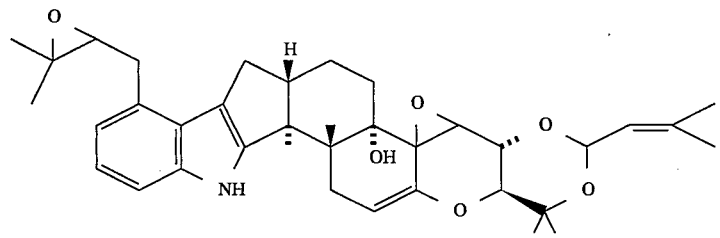

Compound G

The compounds of the present invention may have asymmetric centers and occur as racemates, racemic mixtures and as individual enantiomers or diastereomers, with all isomeric forms and mixtures thereof being included within the scope of the present invention.

When any variable (e.g., aryl, alkyl, $R^1$, $R^2$, etc.) occurs more than one time in any constituent or in a structural formula, its definition on each occurrence is independent of its definition at every occurrence. Also, combinations of substituents and/or variables are permissible only if such combinations result in stable compounds.

Also included within the scope of this invention are pharmaceutically acceptable salts or esters, where a basic or acidic group is present in a compound of formula II, such as, for example on the substituted alkyl moiety. When an acidic substituent is present, i.e. —COOH, there can be formed the ammonium, sodium, calcium salt, and the like, for use as the dosage form. Also, in the case of the —COOH group being present, pharmaceutically acceptable esters may be employed, e.g., acetate, maleate, pivaloyloxymethyl, and the like, and those esters known in the art for modifying solubility or hydrolysis characteristics for use as sustained release or prodrug formulations.

Where a basic group is present, such as amino, acidic salts such as hydrochloride, hydrobromide, acetate, pamoate and the like may be used as the dosage form.

As used herein "alkyl" is intended to include both branched-and straight-chain saturated aliphatic hydrocarbon groups having the specified number of carbon atoms and includes methyl (Me), ethyl (Et), propyl (Pr), butyl (Bu), pentyl, hexyl and the like. "Alkoxy" represents an alkyl group of the indicated number of carbon atoms attached through an oxygen bridge. "Cycloalkyl" is intended to include saturated carbon ring groups such as cyclopropyl, cyclobutyl, cyclopentyl, and cyclohexyl (Cyh). "Alkenyl" is intended to include hydrocarbon groups of either a straight or branched configuration with one or more carbon-carbon double bonds which may occur in any stable point along the chain, such as ethenyl, propenyl, butenyl, and the like. "Alkynyl" is intended to include hydrocarbon groups of either a straight or branched configuration with one or more carbon-carbon triple bonds which may occur in any stable point along the chain, such as ethynyl, propynyl, butynyl, and the like. "Halo" or "halogen" as used herein means fluoro, chloro, bromo and iodo. The term "Boc" refers to t-butyloxy-carbonyl.

Compounds A, B, C, D and G and the related compounds within the scope of the present invention exhibit potassium channel antagonist activity and thus are useful in disorders associated with potassium channel malfunction. A number of cognitive disorders such as Alzheimer's Disease, memory loss or depression may benefit from enhanced release of neurotransmitters such as serotonin, dopamine or acetylcholine and the like. Blockage of Maxi-K channels maintains cellular depolarization and therefore enhances secretion of these vital neurotransmitters.

The claimed compounds are active as potassium channel antagonists or are useful in the production of potassium channel antagonists. Members of the isoxazoline class are produced by a novel process wherein the starting material may be selected from paxilline or any indole diterpene having a hydroxyl group beta to a carbonyl group. Paxilline or a related indole diterpene containing the necessary hydroxyl-carbonyl functionality may be reacted with hydroxylamine in a suitable solvent under appropriate conditions to form the oxime which is further reacted with tributylphosphine and diphenyldisulfide to produce an isoxazoline such as paxizoline. The claimed process is not limited to producing potassium channel antagonists such as paxizoline but may also be used to produce pharmaceutically active isoxazolines or drugs containing an isoxazoline ring. The scheme below indicates the required functionality and describes the general process:

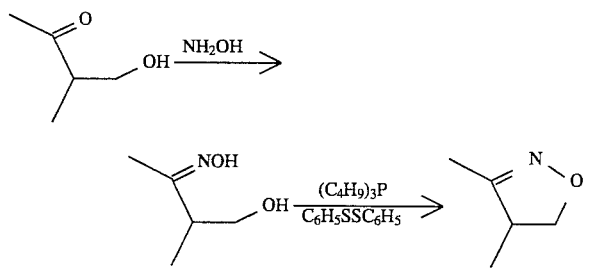

As shown above, the claimed process relates generally to the initial formation of an oxime which subsequently reacts with tributylphosphine and diphenyldisulfide to form the heterocycle isoxazoline or isoxazole.

The free acid groups on the compounds produced by the microbiological process of the instant invention may also be readily modified to the alkyl ester derivatives to produce active potassium channel antagonists. For example, trimethylsilyldiazomethane added to a methanolic solution containing a free acid moiety is readily converted to the methyl ester. Other simple alkyl or aryl or benzyl esters may readily be prepared by conventional means to produce compounds within the scope of the present invention.

The indole nitrogen may readily be protected with a suitable protecting group selected from, for example, t-Butyloxycarbonyl or other protecting group selected from groups described in "Protective Groups in Organic Synthesis" by Greene and Wutts (1991). Furthermore, the free alcohol moieties may also be protected using standard hydroxyl protecting groups to form compounds within the scope of the present invention.

The present invention relates to a fermentation process for producing potassium channel antagonists comprising:

(a) inoculating seed medium (Table 1) with mycelia of *Nalanthalama sp.* MF5785 (ATCC$_{74192}$);

(b) incubating the inoculated mycelia at room temperature (20°–30° C.) under humid conditions with constant fluorescent light, preferably with shaking, most preferably on a rotary shaker with a 5 cm throw at 220 rpm;

(c) using the culture produced in step (b) to inoculate a liquid production medium and further incubating under the conditions defined in step (b) to produce Compounds A, B, C, D and G.

Maximal accumulation of compounds A, B, C, D and G in the fermentation broth occurs between 7–11 days. The invention further comprises a step (d) in which the compounds produced in the fermentation broth under suitable defined and controlled conditions are purified and isolated from the broth. Suitable isolation procedures include, for example, extraction of the culture medium with an alcoholic or oxygenated solvent, such as an ether or ketone, preferably methylethylketone.

The strain MF5785 has been identified as an Nalanthaloma. The fungus was isolated from unidentified twigs collected in the province of Nuevo Leon, Mexico. The generic disposition is based the undifferentiated, unbranched, solitary, enteroblastic, phialidic conidiogenous cells that give rise to conidia that are small, subglobose, hyaline and smooth. Within the genus Acremonium, this isolate could be assigned to the series terricola because the conidia adhere to the conidogenous cells in dry chains. However, the isolate does not match any of the taxa in this series presented by Gams in his monograph of the genus Acremonium (W. Grams. 197 1. *Cephalosporium-artige Schimmelpilze (Hyphomycetes)*. This organism grows well and sporulates abundantly in most mycological media. In agar culture, the strain exhibits the following morphological features:

Colonies growing moderately well on oatmeal agar (Difco Laboratories), 25° C., 12 hr photoperiod, after 21 days attaining 34–36 mm in diameter, slightly raised, velvety, finely cottony, becoming minutely granular at the center, dull, dry, faintly zonateith margin even and submerged, white at the margin becoming dull vinaceous to grayish vinaceous, Pale Vinaceous-Fawn, Vinaceous-Buff, Light Vinaceous-Fawn, to Vinaceous-Fawn (capitalized color names from Ridgway, R. 1912. *Color Standards and Nomenclature*, Washington, D.C.). Odors and exudates absent.

Colonies growing moderately fast on Emerson Yp Ss (Difco Laboratories) agar, 25° C., 12 hr photoperiod, after 21 days attaining 30 mm diameter, appressed to slightly raised, faintly radially sulcate, faintly zonate, velvety, with minute drops of watery exudate towards center, dry, dull, with margin submerged, minute fimbriate to wavy, translucent, white to pale vinaceous, Pale Vinaceous-Fawn, Light Vinaceous-Fawn, translucent to pale yellow in reverse. Odors and exudates absent.

Colonies growing moderately fast on Barnett's oak wilt agar (Barnett, H. L. 1953. Isolation and identification of the oak wilt fungus. West Virginia Agricultural Experiment Station Bulletin 359T: 1–15.), 25° C., 12 hr photoperiod, after 21 days attaining 25 mm diameter, appressed, pruinose to downy, farinaceous towards the center, radially rivulose, faintly zonate, with margin even and submerged, white to pale vinaceous, with farinaceous granules pale vinaceous gray. Granular texture caused by aggregation of conidiophores into small pustules and accumulations of dry conidia. Odors and exudates absent.

No growth occured at 37° C. on Emerson Yp Ss agar after 21 days.

Conidiophores micronematous, occasionally semi-micronematous, integrated, up to 30 μm tall, but usually 6–12 μm tall, branched or not, septate or not, often only a simple right-angle branch from main hyphal axis, usually with a single terminal conidiogenous locus, but occasionally conidiogenous loci are lateral or intercalary. Conidiogenous cells terminal or intercalary, appearing enteroblastic and phialidic, occasionally swollen at the base. Conidia hyaline, thin-walled, broadly ellipsoidal or obovate, with a slightly flattened base, 2–5×15.2.5 μm, accumulating in dry chains, sometime with faint connectives evident.

Hyphae septate, branched, finely incrusted in mature regions of the colonies.

In general, Compounds A, B, C, D and G can be produced by culturing (fermenting) strain MF5785, ATCC74192, in an aqueous nutrient medium containing assimilable carbon and nitrogen sources, preferably under submerged aerobic conditions, and shaking the culture under constant fluorescent light, preferably 450 to 700 nm, until a substantial amount of Compounds A, B, C, D and G is detected in the fermentation broth. The culture is incubated in a aqueous medium at a temperature between 20° C. and 37° C., preferably 25° C. for a period of time necessary to complete the formation of Compounds A, B, C, D,and G, usually for a period between 3 to 28 days, preferably between 7 to 11 days, preferably on a shaking means, most preferably on a rotary shaker operating at 220 rpm with a 5 cm throw. The aqueous production medium is maintained at a pH between 5 and 8, preferably about 6.0, at the initiation and termination (harvest) of the fermentation process. The desired pH may be maintained by the use of a buffer such as [2-(N-morpholino)ethanesulfonic acid] monohydrate (MES), 3-(N-morpholino)propanesulfonic acid (MOPS), phosphate buffer or any other buffer effective in pH 5 to 8, or by choice of nutrient materials which inherently possess buffering properties, such as production media described herein below. The active compound is extracted from the mycelial growth of the culture is with a suitable solvent, such as alcoholic or oxygenated solvent such as an ester or ketone. The preferred solvent for extraction is methylethylketone (MEK). The solution containing the desired compound is concentrated and then subjected to chromatographic separation to isolate compounds A, B, C, D and G from the cultivation medium.

The preferred sources of carbon in the nutrient medium include sucrose, glucose, fructose, mannitol, glycerol, xylose, galactose, lactose, sorbitol, starch, dextrin, other sugars and sugar alcohols, starches and other carbohydrates, or carbohydrates derivatives, and the like. Other sources which may be included are maltose, rhamnose, raffinose, arabinose, mannose, salicin, sodium succinate, acetate, and the like as well as complex nutrients such as yellow corn meal, oat flour, millet, rice, cracked corn, and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium.

The preferred sources of nitrogen are yeast extract, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as methionine, phenylalanine, serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form because less pure materials which contain traces of growth factors and considerable quantities of mineral nutrients are also suitable for use. When desired, them may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0, and trace elements ranging from 0.001 to 0.1 percent by weight of the medium.

If necessary, especially when the culture medium foams seriously, a defoaming agent, such as polypropylene glycol 2000 (PPG- 2000), liquid paraffin, fatty oil, plant oil, mineral oil or silicone may be added.

Submerged aerobic fermentation conditions in fermentors are preferred for the production of Compounds A, B, C, D and G in large amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compounds A, B, C, D and G. Accordingly, it is desirable first to produce a vegetative inoculum of the organism by inoculating a relatively small quantity of culture medium with spores or mycelia of the organism produced in a "slant," or from previously prepared frozen mycelia, and culturing the inoculated medium, also called the "seed medium", and then aseptically transferring the cultured vegetative inoculum to large tanks. The seed medium, in which the inoculum is produced may be seen in Table 1 and is generally autoclaved to sterilize the medium prior to inoculation. The seed medium is generally adjusted to a pH between 5 and 8, preferably about 6.8, prior to the autoclaving step by suitable addition of an acid or base, preferably in the form of a dilute solution of hydrochloric acid or sodium hydroxide. Growth of the culture in this seed medium is maintained between 26° C. and 37° C., preferably 25° C. Incubation of culture MF5785 (ATCC 74192) in a seed medium, preferably that in Table 1, is usually conducted for a period of about 2 to 6 days, preferably 3 to 4 days, with shaking, preferably on a rotary shaker operating at 220 rpm with a 5 cm throw; the length of incubation time may be varied according to fermentation conditions and scales. If appropriate, a second stage seed fermentation may be carried out in the seed medium (Table 1 ) for greater production of mycelial mass by inoculating fresh seed medium with a portion of the culture growth and then incubating under similar conditions but for a shortened period. The resulting growth then may be employed to inoculate, a production medium, preferably the Liquid Production Medium (Table 2). The fermentation liquid production medium inoculated with the seed culture growth is incubated for 3 to 28 days, usually 7 to 11 days, with agitation. Agitation and aeration of the culture mixture may be accomplished in a variety of ways. Agitation may be provided by a propeller or similar mechanical agitation equipment, by revolving or shaking the fermentation mixture within the fermentor, by various pumping equipment or by the passage of sterile air through the medium. Aeration may be effected by passing sterile air through the fermentation mixture.

Preferred seed and production media for carrying out the fermentation include the following media:

TABLE 1

Seed Medium

| | per liter | Trace Element Mix | per liter |
|---|---|---|---|
| Corn Steep Liquor | 5 g | FeSO$_4$.H$_2$O | 1 g |
| Tomato Paste | 40 g | MnSO$_4$.H$_2$O | 1 g |
| Oat flour | 10 g | CuCl$_2$.2H$_2$O | 25 mg |
| Glucose | 10 g | CaCl$_2$ | 100 mg |

TABLE 1-continued

Seed Medium

| | per liter | Trace Element Mix | per liter |
|---|---|---|---|
| Trace element mix | 10 mL | $H_3BO_3$ | 56 mg |
| | | $(NH_4)_6Mo_7O_{24}\cdot 4H_2O$ | 19 mg |
| | | $ZnSO_4\cdot 7H_2O$ | 200 mg | pH = 6.8

TABLE 2

Liquid Production Medium

| Component | Per Liter |
|---|---|
| Yellow Cornmeal | 50.0 g |
| Yeast Extract | 1.0 g |
| Sucrose | 80.0 g |
| Distilled Water | 1000.0 mL |

The following examples are provided to illustrate the present invention and shall not be construed as being limitatives of the scope or spirit of the invention.

EXAMPLE 1

Production of Compounds A, B, C, D and G

Step A: Fermentation Conditions for Production of Compounds A–D and G

Fermentation conditions for the production of Compounds A, B, C, D and G by the microorganism *Nalanthamala sp.* were as follows: vegetative mycelia of a culture of the above microorganism were prepared by inoculating 54 mL of seed medium (Table 1) in a 250 mL unbaffled Erlenmeyer flask with frozen mycelia of MF5785 (ATCC 74192). Seed flasks were incubated at 25° C. and 50% relative humidity on a rotary shaker with a 5 cm throw at 220 rpm in a room with constant fluorescent light, about 400 to 750 nm. Two-mL portions of the resulting 3-day culture were used to inoculate 50 mL portions of Liquid Production Medium (Table 2) in 250 mL unbaffled Erlenmeyer flasks; these cultures were incubated at 25° C., 220 rpm with 50% relative humidity in a room with constant fluoroscent light. The products appeared in the fermentation as early as 7 days with maximal accumulation observed at day 11. At harvest, the compounds were extracted as described below.

Step B: Isolation of Compounds A, B, C, D and G

The fermentation broth of MF5785 (ATCC$_{74192}$), prepared above (3 L WBE; IC$_{50}$=10 μl WBE per mL in [$^{125}$I]ChTX binding assay (described in Example 6) was extracted with methyl ethyl ketone, and the solvent was removed in vacuo. The dry residue was then partitioned between $CH_2Cl_2$ and $H_2O$ to give 4.5 g in organic phase. The aqueous phase was treated with methanol after the water was removed to yield 1.6 g. The organic phases were subjected to flash chromatography on $SiO_2$ using $CH_2Cl_2$-$CH_3OH$ to result in two fractions, I (2.36 g) and II (1.97 g). Reverse phase flash chromatography on B AKERBOND $C_{18}$ using methanol-water on each fraction was followed by HPLC on PARTISIL 10 ODS-3 (22×50; flow rate 10 mL per min).

The fraction I yielded several compounds in different amounts upon purification by HPLC (70% $CH_3CN$-$H_2O$) as follows:

Compound A ($C_{32}H_{43}NO_3$, M.W. 489.3243 (calcd), 489.3226 (found)) of the chemical formula:

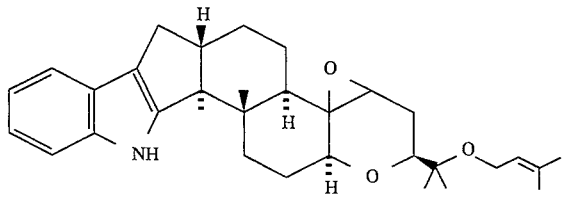

Compound B ($C_{37}H_{51}NO_5$, M.W. 589.3767 (calcd), 589.3749 (found)) of the chemical formula:

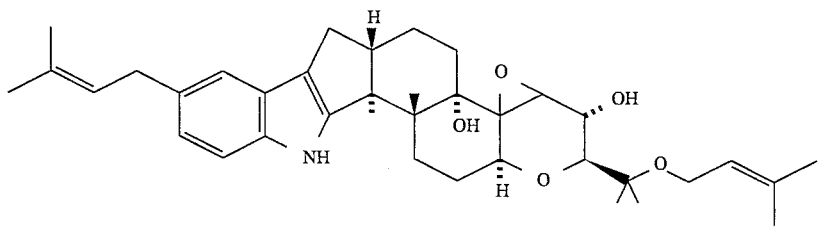

Compound C ($C_{37}H_{47}NO_5$, M.W. 585.3506 (calcd), 585.3454 (found)) of the chemical formula:

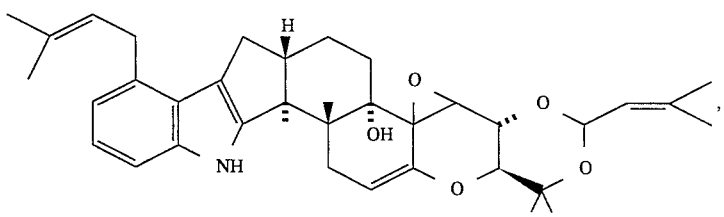

Compound C

The fraction II provided hydroxypaspalinic acid (Compound D) upon HPLC (50% $CH_3OH$-$H_2O$) and Compound G:

Compound D (29.2 mg; $C_{28}H_{37}NO_5$; M.W. 467.2672 (calcd), 467.2641 (found)) of the chemical formula:

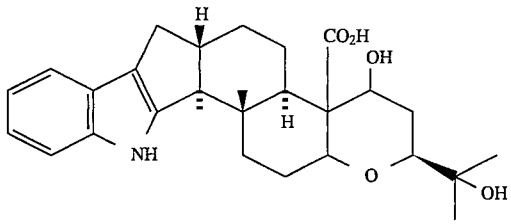

Compound G ($C_{37}H_{49}NO_6$; M.W. 603.3559 (calcd))

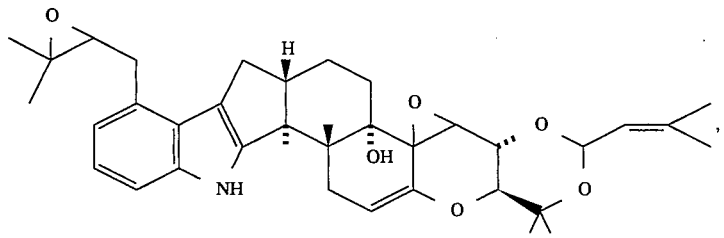

$^{13}$C NMR Data $^{13}$C NMR spectra were recorded in $CD_2Cl_2$ and $CD_3OD$ at 125 MHz on Varian Unity 500 NMR spectrometer at 25° C. Chemical shifts are given in ppm relative to tetramethylsilane (TMS) at zero ppm using the solvent peak at 53.8 ($CD_2Cl_2$) and 49.0 ($CD_3OD$) ppm as internal standard.

Compound A ($CD_2Cl_2$): 16.0, 17.9, 18.0, 18.7, 19.2, 21.0, 23.7, 25.77, 25.81, 27.5, 27.7, 28.1, 30.8, 34.8, 42.7, 50.4, 51.0, 58.4, 64.9, 67.5, 69.1, 71.8, 75.3, 78.2, 79.5, 111.1, 117.6, 118.4, 120.8, 121.2, 123.7, 124.6, 132.0, 134.6, 137.4, 140.6, 151.8 ppm. The carbon count of 37 is in agreement with the HR-EIMS derived molecular formula $C_{37}H_{51}NO_5$.

Compound B ($CD_2Cl_2$): 14.6, 16.6, 18.0, 21.3, 22.4, 23.3, 24.5, 25.8, 26.6, 27.5, 29.7, 32.9, 39.8, 41.3, 50.0, 50.7, 56.2, 59.1, 61.8, 73.89, 73.97, 76.0, 111.7, 118.5, 118.6, 119.8, 120.7, 122.9, 125.4, 135.1, 140.3, 150.5 ppm. The carbon count of 32 is in agreement with the HR-EIMS derived molecular formula $C_{32}H_{43}NO_3$.

Compound C ($CD_2Cl_2$): 16.2, 16.8, 18.0, 18.7, 20.1, 20.8, 25.6, 25.8, 28.1, 29.4, 30.8 (2 x), 32.3, 44.1, 50.4, 50.7, 60.7, 65.2, 71.4, 73.9, 75.0, 76.6, 93.2, 106.3, 109.5, 117.2, 119.3, 121.2, 122.2, 124.2, 124.9, 132.1, 133.4, 139.8, 140.2, 144.9, 151.3 ppm. The carbon count of 37 is in agreement with the HR-EIMS derived molecular formula $C_{37}H_{47}NO_5$.

Compound D ($CD_3OD$): 14.8, 16.9, 24.7, 25.4, 26.1, 26.2, 26.3, 28.3, 32.3, 33.9, 40.8, 41.5, 50.3, 53.5, 53.7, 68.3, 72.6, 77.6, 79.7, 112.6, 118.0, 118.7, 119.7, 120.7, 126.2, 142.1, 152.1, 178.1 ppm. The carbon count of 28 is in agreement with the HREI-MS derived molecular formula $C_{28}H_{37}NO_5$.

Compound G ($CD_2Cl_2$): 16.0, 16.8, 18.7, 18.9, 19.1, 20.9, 25.0, 25.6, 27.7, 28.35, 28.44, 29.4, 30.7, 33.1, 42.7, 50.6, 50.7, 58.8, 61.5, 64.6, 68.2, 71.4, 71.7, 72.0, 74.9, 78.5, 93.0, 110.2, 117.0, 119.7, 121.1, 122.6, 125.1, 129.6, 139.3, 140.0, 151.9 ppm. The NMR data indicates a carbon count of 37 and a molecular formula $C_{37}H_{47}NO_6$.

$^1$H NMR Data $^1$H NMR spectra were recorded at 500 MHz in $CD_2Cl_2$ Varian XL300 on a Unity 500 NMR spectrometer at 250C and in $CD_3OD$ for Compound D at 300 MHz on a Varian XL300 spectrometer at ambient temperature. Chemical shifts are indicated in ppm relative to TMS at zero ppm using the solvent peak at δ55.32 ($CD_2Cl_2$) and 3.30 ($CD_3OD$) as internal standard. Only diagnostic peaks are noted.

Compound A ($CD_2Cl_2$): δ1.11 (3 H, s), 1.22 (3 H, s), 1.25 (3 H, s), 1.28 (3 H, s), 1.66 (3 H, br s), 1.73 (3 H, br s), 1.74 (6 H, br s), 1.91 (1 H, m), 2.03 (1 H, m), 2.26 (1 H, m), 2.36 (1 H dd, J=11, 13 Hz), 2.66 (1 H, dd, J=6.5, 13 Hz), 2.79 (1 H, m), 3.34 (1 H, d, J=9 Hz), 3.38 (2 H, m), 3.56 (1 H, br s), 3.96 (3 H, m), 4.17 (1 H, t, J=8.5 Hz), 5.26 (1 H, m), 5.35 (1 H, m), 6.86 (1 H, rid, J=1.5, 8 Hz), 7.09 (1 H, br s), 7.17 (1 H, d, J= 8 Hz), 7.74 (1 H, br s, NH).

Compound G

Compound B ($CD_2Cl_2$) : 15 1.02 (3 H, s), 1.08 (3 H, s), 1.11 (3 H, s), 1.14 (3 H, s), 1.64 (3 H, br s), 1.72 (3 H, br s), 1.86 (1 H, m), 1.94 (1 H, m), 2.09 (1 H, m), 2.25 (1 H, m), 2.37 (1 H, dd, J=10.5, 13.5 Hz), 2.68 (1 H, dd, J=6.5, 13.5 Hz), 2.79 (1 H, m), 3.42 (1 H, br d, J=3 Hz), 3.66 (1 H, dd, J=2.5, 11 Hz), 3.88 (1 H, m), 3.96 (1 H, m), 5.25 (1 H, m), 5.35 (1 H, m), 7.02 (1 H, dt, J=1.5, 7 Hz), 7.05 (1 H, dt, J=1.5, 7 ), 7.30 (1 H, m), 7.39 (1 H, m), 7.88 (1 H, br s, NH).

Compound C ($CD_2Cl_2$): δ1.17 (3 H, s), 1.30 (3 H, s), 1.31 (3 H, s), 1.32 (3 H, s), 1.71 (3 H, d, J~1.5 Hz), 1.74 (6 H, d, J~1 Hz), 1.76 (3 H, d, J~1 Hz), 1.67 (1 H, m), 1.88 (1 H, dd, J=7, 16 Hz), 1.95 (1 H, m), 2.57 (1 H, dd, J=10.5, 13.0 Hz), 2.77 (1 H, m), 2.84 (1 H, dd, J=6.5, 13.0 Hz), 3.18 (1 H, br d, J~16 Hz), 3.58 (1 H, br d, J=7 Hz), 3.86 (1 H, s), 3.96 (1 H, d, J=10 Hz), 4.00 (1 H, d, J=10 Hz), 5.21 (1 H, m), 5.35 (1 H, m), 5.39 (1 H, dd, J=2, 7 Hz), 5.47 (1 H, d, J=6.5 Hz), 6.81 (1 H, dd, J=1, 7 Hz), 6.96 (1 H, dd, J=7, 8 Hz ), 7.14 (1 H, dd, J=1, 8 Hz), 7.83 (1 H, br s, NH).

Compound D ($CD_3OD$ at 300 MHz): ~5 1.01 (3 H, s), 1.09 (3 H, s), 1.12 (3 H, s), 1.20 (3 H, s), 2.21 (1 H,dd, J=4, 12 Hz), 2.29 (1 H, dd, J=10.5, 13.0 Hz), 2.61 (1 H, dd, J=6.5, 13.0 Hz), ~2.73 (1 H, m), 3.64 (1 H, dd, J=3, 11 Hz), 3.67 (1 H, dd, J=4.5, 12 Hz), 4.37 (1 H, t, J=~3 Hz), 6.92 (2 H, m), 7.27 (2 H, m).

Compound G ($CD_2Cl_2$): d 1.15 (3 H, s), 1.24 (3 H, s), 1.27 (3 H, s), 1.28 (3 H, s), 1.31 (3 H, s), 1.40 (3 H, s), 1.71 (3 H, d, J=1 Hz), 1.74 (3 H, d, J=1 Hz), 1.81 (1 H, m), 1.93 (1 H, m), 2.27 (1 H, m), 2.59 (1 H, dd, J=13, 15 Hz), 2.69 (1 H, dt, J=5, 13.5 Hz), 2.84 (2 H, m), 3.14 (2 H, m), 3.16 (1 H, m), 3.49 (1 H, d, J=9.5 Hz), 3.59 (1 H, s), 3.91 (1 H, dd, J=1, 9.5 Hz), 4.32 (1 H, br t, J~9 Hz), 5.20 (1 H, m), 5.50 (1 H, d, J=6.5 Hz), 6.87 (1 H, dd, J=1, 7.5 Hz), 7.00 (1 H, dd, J=7.5, 8 Hz ), 7.19 (1 H, dd, J=1, 8 Hz), 7.93 (1 H, br s, NH).

Abbreviations: s=singlet, d=doublet, q=quartet, br=broad, m=multiplet, J=$^1$H-$^1$H coupling constant in Hertz (+0.5 Hz).

EXAMPLE 2

Preparation of Methyl Hydroxypaspalinate, Compound E

To a methanolic solution of the hydroxypaspalinic acid (Compound D, 7.8 mg, 0.016 mM) was added (trimethylsilyl) diazomethane ((CH$_3$)$_3$SiCHN$_2$, 2M solution in hexanes) in excess. The mixture was stirred at room temperature until the faint yellow color dissipated. The solvent was then removed under nitrogen to give the methyl ester (TLC$_5$ % CH$_3$OH-CH$_2$Cl$_2$, R$_f$ 0.19 (acid), 0.39 (ester)). It was purified by HPLC on PARTISIL 10 ODS-3 (22×50) using 60% CH$_3$CN-H$_2$O (flow rate 10 mL per min) to afford methyl hydroxypaspalinate (Compound E; M.W. 481 ). It was eluted at 149.6 min. and has the following formula:

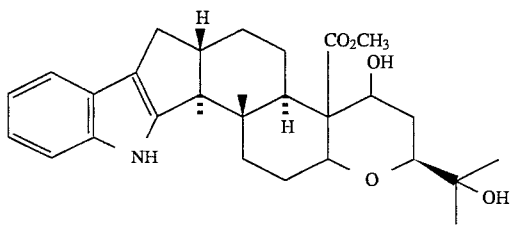

$^{13}$C NMR spectrum was recorded in CD$_3$OD at 75 MHz on a Varian XL300 NMR spectrometer at ambient temperature. Chemical shifts are given in ppm relative to tetramethylsilane (TMS) at zero ppm using the solvent peak at 49.0 (CD$_3$OD) ppm as internal standard. 14.8, 16.6, 24.6, 25.4, 25.9, 26.0, 26.2, 28.3, 32.5, 33.7, 40.6, 41.6, 50.3, 51.5, 53.7, 53.8, 68.1, 72.6, 77.1, 79.4, 112.6, 118.0, 118.7, 119.7, 120.7, 126.2, 142.1, 151.9, 176.2 ppm. The carbon count of 29 and chemical shift positions are consistent with its assignment as the methyl ester of Compound D.

$^1$H NMR spectrum was recorded at 300 MHz in CD$_3$OD on a Varian XL300 spectrometer at ambient temperature. Chemical shifts are indicated in ppm relative to TMS at zero ppm using the solvent peak at δ3.30 (CD$_3$OD) as internal standard. Only diagnostic peaks are noted. δ0.96 (3 H, s), 1.00 (3 H, s), 1.12 (3 H, s), 1.16 (3 H, s), 1.42 (1 H, ddd, J=2.5, 12, 14 Hz), 1.91 (2 H, m), 2.22 (1 H, m), 2.28 (1 H, dd, J=10.5, 13.0 Hz), ~2.59 (1 H, m), 2.60 (1 H, dd, J=6.5, 13.0 Hz), ~2.69 (1 H, m), 3.62 (1 H, dd, J=2, 12 Hz), 3.65 (3 H, s), 3.68 (1 H, dd, J=4.0, 12 Hz), 4.35 (1 H, t, J =~3 Hz), 6.92 (2 H, m), 7.26 (2 H, m).

EXAMPLE 3

Synthesis of Paxizoline, Compound F

Crystalline NH$_2$OH.HCl (32 mg, 0.45 mM) was added to a solution of paxilline (20 mg, 0.045 mM) in Cl$_2$ H$_5$OH (2 mL). The mixture was flushed with nitrogen and stirred until the reaction, monitored by TLC (SiO$_2$, 10% CH$_3$OH-CH$_2$Cl$_2$; R$_f$ 0.67 (ketone) and 0.56 (oxime)), was complete. The solvent was removed, then the residue was transferred to a separatory funnel using ether (5 mL). The organic layer was washed consecutively with water (3×1 mL), saturated aqueous NaCl (1×1 mL), then dried with anhydrous MgSO$_4$, filtered through a sintered glass. The solvent was removed in vacuo. The crude mixture was purified by TLC (SiO$_2$ 60 F-254, 5% CH$_3$OH-CH$_2$Cl$_2$) to give paxilline oxime (18.6 mg; C$_{27}$ H$_{34}$O$_4$N$_2$, M.W. 450.2518 (calcd), 450.25 17 (found)).

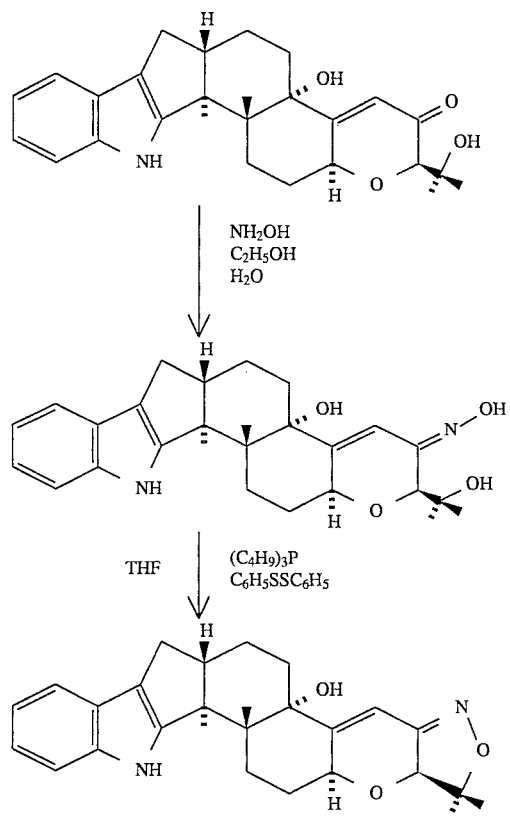

To a mixture of paxilline oxime (10 mg, 0.022 mM) and diphenyl disulfide (4.85 mg, 0.022 mM) in dry tetrahydrofuran (2 ml) was added tributylphosphine (9 mg, 0.044 mM). The mixture was stirred at room temperature overnight under nitrogen, then the solvent was removed. The crude product was purified by HPLC on PARTISIL 10 ODS-3 (9.4×50) using 70% CH$_3$OH-H$_2$O (flow rate 3 mL per min) to give Compound F; 7.5 mg, C$_{27}$ H$_{32}$N$_2$O$_3$, M.W. 432.2413 (calcd), 432.2403 (found), UV (CH$_3$OH) $\lambda_{max}$ (nm) 234, 263, $\lambda_{min}$ 252).

$^{13}$C NMR(CD$_2$Cl$_2$) 75 MHz on Varian XL300 NMR spectrometer at ambient temperature. Chemical shifts are given in ppm relative to tetramethylsilane (TMS) at zero ppm using the solvent peak at 53.8 (CD$_2$Cl$_2$) ppm as internal standard: 16.3, 19.9, 20.3, 21.3, 25.3, 27.4, 28.5, 28.8, 35.1, 43.3, 50.0, 51.1, 74.9, 78.3, 85.8, 86.2, 109.0, 111.7, 117.5, 118.6, 119.8, 120.7, 125.5, 140.1, 152.4, 154.6, 155.2 ppm. The NMR data indicates a carbon count of 27 consistent with the molecular formula C$_{27}$ H$_{32}$N$_2$O$_3$.

$^1$H NMR spectrum was recorded at 300 MHz in CD$_2$Cl$_2$ on a Varian XL300 spectrometer at ambient temperature. Chemical shifts are indicated in ppm relative to TMS at zero ppm using the solvent peak at δ5.32 (CD$_2$Cl$_2$) as internal standard. Only diagnostic peaks are noted. δ 1.02 (3 H, s), 1.20 (3 H, s), 1.33 (3 H, s), 1.53 (3 H, s), 1.90 (1 H, m), 2.24 (1 H, m), 2.43 (1 H, dd, J=11, 13 Hz), 2.73 (1 H, dd, J=6.5, 13 Hz), ~2.74 (1 H, m), 2.86 (1 H, m), 4.54 (1 H, s), 4.87 (1 H, ddd, J=2.5, 7, 10 Hz), 6.31 (1 H, d, J - 2 Hz), 7.03 (2 H, m), 7.30 (1 H, m), 7.40 (1 H, m), 7.86 (1 H, br s, NH).

EXAMPLE 4

Electrophysiological Experiments

Methods:

Patch clamp recordings of currents flowing through large-conductance calcium-activated potassium (maxi-K) channels were made from membrane patches excised from cultured bovine aortic smooth muscle cells using conventional techniques (Hamill et al., 1981, Pflügers Archiv. 391, 85–100) at room temperature. Glass capillary tubing (Gamer #7052) was pulled in two stages to yield micropipettes with tip diameters of approximately 1–2 microns. Pipettes were typically filled with solutions containing (mM): 150 KCl, 10 Hepes (4-(2-hydroxyethyl)- 1-piperazine ethanesulfonic acid), 1 Mg, 0.01 Ca, and adjusted to pH 7.20 with 3.7 mM KOH. After forming a high resistance (> $10^9$ ohms) seal between the sarcolemmal membrane and the pipette, the pipette was withdrawn from the cell, forming an excised inside-out membrane patch. The patch was excised into a bath solution containing (mM): 150 KCl, 10 Hepes, 5 EGTA (ethylene glycol bis(13-aminoethyl ether)-N,N,N',N'-tetraacetic acid), sufficient Ca to yield a free Ca concentration of 1–5 µM, and the pH was adjusted to 7.2 with 10.5 KOH. For example, 4.568 mM Ca was added to give a free concentration of 2 µM at 22 °C. An AXOPATCH 1C amplifier (Axon Instruments, Foster City, Calif.) with a CV-4 headstage was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2M KCl. Maxi-K channels were identified by their large single channel conductance (~250 pS) and sensitivity of channel open probability to membrane potential and intracellular calcium concentration.

Data were stored on a RACAL STORE 4DS FM tape recorder (Racal Recorders, Vienna, Va.) or on digital video tape using a video casette recorder after digitizing the signal with VR-10 (Instrutech Corp., Belmont N.Y.) PCM video encoder. The signal was also recorded on chart paper with a GOULD 2400S chart recorder (Gould Inc., Cleveland Ohio). For quantitative analysis, the data was played into a $DEC_{11-73}$ (Digital Equipment Corp., Maynard, Mass.) after digitization with a DT2782-8D1A analogue to digital converter (Data Translation Inc., Marlboro, Mass.), or played into a Mac IIx or Quadra 700 computer (Apple Computers) after digitization with an ITC-16 interface (Instrutech Corp., Belmont, N.Y.).

Results:

The effects of the compounds of the present invention on maxi-K channels from bovine aortic smooth muscle were examined in excised inside-out membrane patches. Addition of 10 nM Compound C to the bath produced a rapid and complete block of maxi-K channels that was not reversed during a brief (~10 min) washout. 1 nM of Compound B caused nearly complete block of maxi-K channels suggesting a $K_i$ of less than 1 nM for channel block. Compound D, Compound A and Compound E were weaker blockers of maxi-K channels than Compound C. 10 nM Compound D caused less than a 50% reduction in channel open probability, and complete block was not observed at 1 µM. 10 nM of Compound A blocked a small fraction of channel activity, 100 nM blocked approximately one half of the channel activity, and 1 µM blocked nearly all of the channel activity. 1 µM Compound E had no significant effect on channel open probability, while 10 µM caused an incomplete block of channel activity slowly increasing over 5–10 minutes. Compound F caused approximately a 50% decrease in channel activity at 10nM. Compound G at 0.1 nM blocked 82% of channnles,; at 1 nM blocked 98.6%, and at 10 nm caused>99% block. The data is summarized in the table below:

| COMPOUND | [50% CHANNEL BLOCK] |
|---|---|
| A | 100 nm (approx.) |
| B | <1 nM |
| C | <10 nM |
| D | 1 µM (approx.) |
| E | >10 µM |
| F | 10 nM (approx.) |
| G | <0.1 nM (approx.) |

EXAMPLE 6

Biochemical Experiments

Methods:

The interaction of [$^{125}$I]ChTX with bovine aortic s sarcolemma membrane vesicles was determined under conditions as described (Vazquez et al., 1989, J. Biol. Chem. 264, 20902–20909). Briefly, sarcolemma membrane vesicles were incubated in 12×75 polystyrene tubes with ca. 25 pM [$^{125}$I]ChTX (2200 Ci/mmol), in the absence or presence of test compound, in a media consisting of 20 mM NaCl, 20 mM Tris-HCl pH 7.4, 0.1% bovine serum albumin, 0.1% digitonin. Nonspecific binding was determined in the presence of 10 nM ChTX. Incubations were carried out at room temperature until ligand binding equilibrium is achieved at ca. 90 min. At the end of the incubation period, samples were diluted with 4 mL ice-cold 100 mM NaCl, 20 mM Hepes-Tris pH 7.4 and filtered through GF/C glass fiber filters that have been presoaked in 0.5% polyethylenimine. Filters were rinsed twice with 4 mL ice-cold quench solution. Radioactivity associated with filters was determined in a gamma counter. Specific binding data in the presence of each compound (difference between total binding and nonspecific binding) was assessed relative to an untreated control.

Results:

Compound D (hydroxypaspalinic acid) did not have any effect on binding in the range of concentrations from 1 nM to 100 µM. Compound E (methylhydroxypaspalinate) did not affect [$^{125}$I]ChTX binding from 1 nM to 100 µM. Compound A and Compound C inhibited binding by 2 and 29%, respectively, when tested at 10 µM.

The effect of Compound F, paxizoline, was investigated by increasing the concentration of compound in the assay from 1 nM to 100 µM. This compound produced two opposite effects on toxin binding. In the range of 50 nM to 2 µM, there was a small increase in the amount of toxin bound to its receptor. At concentrations above 5 µM, Compound F caused a concentration-dependent inhibition of binding. It appears that the maximum level of inhibition saturates at ca. 32% control.

Compound G inhibited binding by 35% at 10µM.

The previous examples illustrate but do not limit the claimed invention. Each of the purified compounds shown above that is produced via the microbiological production process and the compounds produced synthetically via the novel isoxazoline production process are potassium channel antagonists and are thus useful in those disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

What is claimed is:

1. A compound of formula (I):

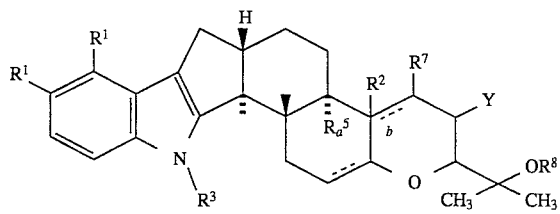

which is

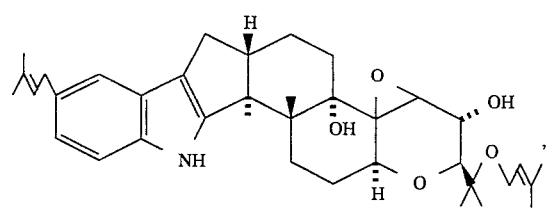

(a)

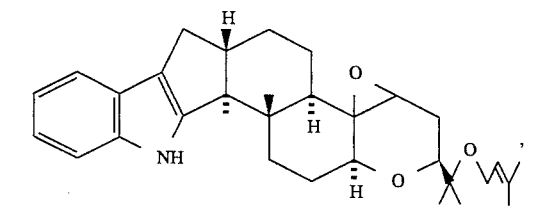

(b)

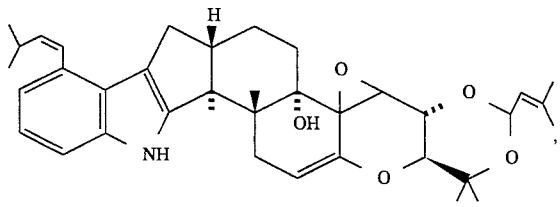

(c)

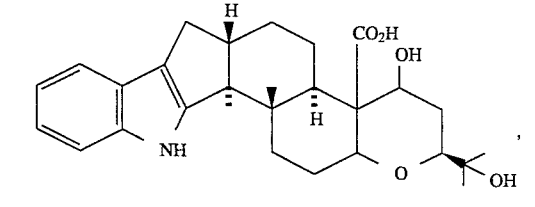

(d)

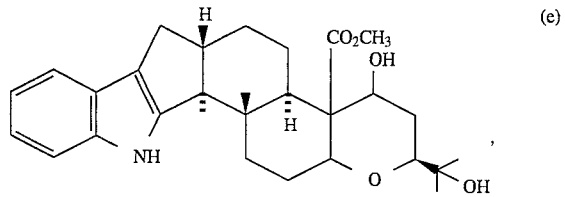

(e)

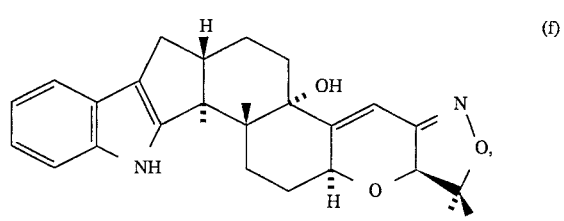

(f)

and

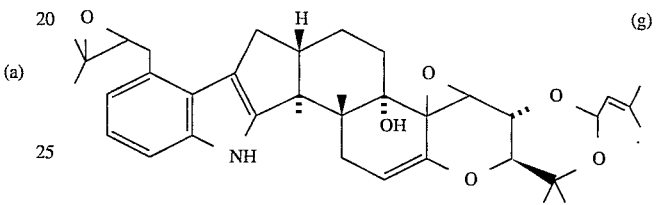

(g)

2. A pharmaceutical composition comprising a compound according to claim 1 and a pharmaceutically acceptable carrier.

3. A method of preventing repolarization or hyperpolarization of a mammalian cell wherein the cell contains a potassium channel comprising the administration to a mammal, in need thereof, of a pharmacologically effective amount of a potassium channel antagonist according to claim 1.

4. A method of treating Alzheimer's Disease in a patient in need thereof comprising administering a pharmaceutically effective amount of a compound according to claim 1.

5. A method of treating depression in a patient in need thereof comprising administering a pharmaceutically effective amount of a compound according to claim 1.

6. A method of treating cognitive disorders in a patient in need thereof comprising administering a pharmaceutically effective amount of a compound according to claim 1.

* * * * *